US009852505B2

(12) United States Patent
Bradley (10) Patent No.: US 9,852,505 B2
(45) Date of Patent: Dec. 26, 2017

(54) SYSTEMS AND METHODS FOR OBSERVING AND ANALYZING SWALLOWING

(71) Applicant: Stuart Bradley, Apex, NC (US)

(72) Inventor: Stuart Bradley, Apex, NC (US)

( * ) Notice: Subject to any disclaimer, the term of this patent is extended or adjusted under 35 U.S.C. 154(b) by 0 days.

(21) Appl. No.: 15/594,564

(22) Filed: May 13, 2017

(65) Prior Publication Data
US 2017/0337684 A1 Nov. 23, 2017

Related U.S. Application Data

(60) Provisional application No. 62/337,922, filed on May 18, 2016.

(51) Int. Cl.
*G06T 7/00* (2017.01)
*G06T 7/90* (2017.01)
*A61B 1/04* (2006.01)
*A61B 1/267* (2006.01)
*A61B 5/00* (2006.01)
*G06T 11/60* (2006.01)
*H04N 5/232* (2006.01)
*H04N 5/225* (2006.01)

(52) U.S. Cl.
CPC .............. *G06T 7/0012* (2013.01); *A61B 1/04* (2013.01); *A61B 1/267* (2013.01); *A61B 5/4205* (2013.01); *G06T 7/90* (2017.01); *G06T 11/60* (2013.01); *H04N 5/23293* (2013.01); *G06T 2207/10016* (2013.01); *G06T 2207/10024* (2013.01); *G06T 2207/10068* (2013.01); *H04N 5/2256* (2013.01); *H04N 2005/2255* (2013.01)

(58) Field of Classification Search
CPC ......... G06T 7/0012; G06T 7/90; G06T 11/60; G06T 2207/10016; G06T 2207/10024; G06T 2207/10068; A61B 1/04; A61B 1/267; A61B 5/4205; H04N 5/23293; H04N 5/2256; H04N 2005/2255
USPC .......................................................... 348/70
See application file for complete search history.

(56) References Cited

U.S. PATENT DOCUMENTS

| 5,976,084 A * | 11/1999 | Tymchuck | A61B 5/00 128/898 |
| 6,050,938 A | 4/2000 | Creed et al. | |
| 2005/0075551 A1* | 4/2005 | Horn | A61B 1/00009 600/361 |
| 2005/0124888 A1* | 6/2005 | Jjt Rein | A61B 8/481 600/443 |

(Continued)

OTHER PUBLICATIONS

International Search Report and Written Opinion issued in PCT Application No, PCT/US2017/032568 dated Jul. 12, 2017.

*Primary Examiner* — Jay Patel
*Assistant Examiner* — Marnie Matt
(74) *Attorney, Agent, or Firm* — Olive Law Group, PLLC (57) ABSTRACT

A system is disclosed that includes an intubating scope and image capture device configured to capture one or more images of an interior of a subject's throat during swallowing of bolus. The system also includes a computing device configured to receive the captured one or more images. The computing device is also configured to analyze the image(s) to measure an amount of tissue covered by bolus in the one or more images. Further, the computing device is configured to present information indicating the measure of the amount of tissue covered by bolus.

23 Claims, 7 Drawing Sheets (56) References Cited

U.S. PATENT DOCUMENTS

| | | | |
|---|---|---|---|
| 2005/0283064 A1 | 12/2005 | Gross et al. | |
| 2006/0069317 A1* | 3/2006 | Horn | A61B 5/065 600/300 |
| 2006/0169294 A1* | 8/2006 | Kaler | A61B 5/073 128/899 |
| 2006/0232668 A1* | 10/2006 | Horn | A61B 1/041 348/71 |
| 2007/0287891 A1* | 12/2007 | Horn | A61B 1/00016 600/300 |
| 2007/0299309 A1* | 12/2007 | Seibel | A61B 1/0008 600/117 |
| 2010/0265251 A1* | 10/2010 | Vining | G06T 7/11 345/420 |
| 2011/0046458 A1* | 2/2011 | Pinedo | A61B 5/07 600/309 |
| 2012/0089045 A1* | 4/2012 | Seidl | A61B 5/053 600/547 |
| 2013/0231533 A1 | 9/2013 | Papademetriou et al. | |

* cited by examiner

SYSTEMS AND METHODS FOR OBSERVING AND ANALYZING SWALLOWING

CROSS REFERENCE TO RELATED APPLICATION

This application claims priority to U.S. Provisional Patent Application 62/337,922, titled SYSTEMS AND METHODS FOR OBSERVING AND ANALYZING SWALLOWING, and filed May 18, 2016, the content of which is incorporated herein by reference in its entirety.

TECHNICAL FIELD

The present subject matter relates to medical imaging and analysis. More specifically, the present subject matter relates to systems and methods for observing and analyzing swallowing.

BACKGROUND

Dysphagia is a disorder in which the sufferer has difficulty swallowing. This means that it requires the individual more time and effort to move food or liquid from the mouth to the stomach. Dysphagia may be associated with pain, and in some cases swallowing may be impossible necessitating feeding tubes and/or intravenous hydration and nutrition. There are three phases of swallowing: oral, pharyngeal, and esophageal. A problem may arise during any one of the phases. Problems during the pharyngeal phase include having a hard time starting a swallow; getting food or liquid into the airway (aspiration); and having some food or liquid stay in the throat after swallowing, referred to as residue.

Medical practitioners, such as speech-language pathologists, can work with individuals having swallowing problems. They can observe an individual's swallowing attempts by the use of an endoscope for viewing an interior of the individual's throat. The endoscope may be configured with a camera for capture of images and video of the interior of the throat to thereby allow the medical practitioner to view the throat interior on a display. Although current endoscopes with cameras are very useful for observing swallowing, there is a desire for improved endoscopy systems for assisting a medical practitioner with analysis of an individual's swallowing attempts.

SUMMARY

Disclosed herein are systems and methods for observing and analyzing swallowing. According an aspect, a system includes an intubating scope and image capture device configured to capture one or more images of an interior of a subject's throat during swallowing of bolus (e.g., food and/or liquid). The system also includes a computing device configured to receive the captured one or more images. The computing device is also configured to analyze the image(s) to measure an amount of tissue covered by bolus in the one or more images. Further, the computing device is configured to present information indicating the measure of the amount of tissue covered by bolus.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The illustrated embodiments of the disclosed subject matter will be best understood by reference to the drawings, wherein like parts are designated by like numerals throughout. The following description is intended only by way of example, and simply illustrates certain selected embodiments of devices, systems, and processes that are consistent with the disclosed subject matter as claimed herein.

DETAILED DESCRIPTION

The following detailed description is made with reference to the figures. Exemplary embodiments are described to illustrate the disclosure, not to limit its scope, which is defined by the claims. Those of ordinary skill in the art will recognize a number of equivalent variations in the description that follows.

The functional units described in this specification have been labeled as computing devices. A computing device may be implemented in programmable hardware devices such as processors, digital signal processors, central processing units, field programmable gate arrays, programmable array logic, programmable logic devices, cloud processing systems, or the like. The computing devices may also be implemented in software for execution by various types of processors. An identified device may include executable code and may, for instance, comprise one or more physical or logical blocks of computer instructions, which may, for instance, be organized as an object, procedure, function, or other construct. Nevertheless, the executable of an identified device need not be physically located together, but may comprise disparate instructions stored in different locations which, when joined logically together, comprise the computing device and achieve the stated purpose of the computing device.

An executable code of a computing device may be a single instruction, or many instructions, and may even be distributed over several different code segments, among different applications, and across several memory devices. Similarly, operational data may be identified and illustrated herein within the computing device, and may be embodied in any suitable form and organized within any suitable type of data structure. The operational data may be collected as a single data set, or may be distributed over different locations including over different storage devices, and may exist, at least partially, as electronic signals on a system or network.

The described features, structures, or characteristics may be combined in any suitable manner in one or more embodiments. In the following description, numerous specific details are provided, to provide a thorough understanding of embodiments of the disclosed subject matter. One skilled in the relevant art will recognize, however, that the disclosed subject matter can be practiced without one or more of the specific details, or with other methods, components, materials, etc. In other instances, well-known structures, materials, or operations are not shown or described in detail to avoid obscuring aspects of the disclosed subject matter.

As referred to herein, the term "user interface" is generally a system by which users interact with a computing device. A user interface can include an input for allowing users to manipulate a computing device, and can include an output for allowing the computing device to present information and/or data, indicate the effects of the user's manipulation, etc. An example of a user interface on a computing device includes a graphical user interface (GUI) that allows users to interact with programs or applications in more ways than typing. A GUI typically can offer display objects, and visual indicators, as opposed to text-based interfaces, typed command labels or text navigation to represent information and actions available to a user. For example, a user interface can be a display window or display object, which is selectable by a user of a computing device for interaction. In another example, the user can use any other suitable user interface of a computing device, such as a keypad, to select the display icon or display object. For example, the user can use a track ball or arrow keys for moving a cursor to highlight and select the display object.

As used herein, the term "memory" is generally a storage device of a computing device. Examples include, but are not limited to, ROM and RAM.

The device or system for performing one or more operations on a memory of a computing device may be a software, hardware, firmware, or combination of these. The device or the system is further intended to include or otherwise cover all software or computer programs capable of performing the various heretofore-disclosed determinations, calculations, or the like for the disclosed purposes. For example, exemplary embodiments are intended to cover all software or computer programs capable of enabling processors to implement the disclosed processes. Exemplary embodiments are also intended to cover any and all currently known, related art or later developed non-transitory recording or storage mediums (such as a CD-ROM, DVD-ROM, hard drive, RAM, ROM, floppy disc, magnetic tape cassette, etc.) that record or store such software or computer programs. Exemplary embodiments are further intended to cover such software, computer programs, systems and/or processes provided through any other currently known, related art, or later developed medium (such as transitory mediums, carrier waves, etc.), usable for implementing the exemplary operations disclosed below.

In accordance with the exemplary embodiments, the disclosed computer programs can be executed in many exemplary ways, such as an application that is resident in the memory of a device or as a hosted application that is being executed on a server and communicating with the device application or browser via a number of standard protocols, such as TCP/IP, HTTP, XML, SOAP, REST, JSON and other sufficient protocols. The disclosed computer programs can be written in exemplary programming languages that execute from memory on the device or from a hosted server, such as BASIC, COBOL, C, C++, Java, Pascal, or scripting languages such as JavaScript, Python, Ruby, PHP, Perl, or other suitable programming languages.

As referred to herein, the term "computing device" should be broadly construed. It can include any type of computing device, for example, a smart phone, a cell phone, a pager, a personal digital assistant (PDA, e.g., with GPRS NIC), a mobile computer with a smartphone client, or the like. A computing device can also include any type of conventional computer, for example, a desktop computer or a laptop computer. A typical mobile device is a wireless data access-enabled device (e.g., an iPHONE® smartphone, a BLACKBERRY® smart phone, a NEXUS ONE™ smart phone, an iPAD™ device, or the like) that is capable of sending and receiving data in a wireless manner using communications protocols such as the Internet Protocol (IP), BLUETOOTH®, WI-FI®, and the wireless application protocol (WAP). This allows users to access information via wireless devices, such as smart phones, mobile phones, pagers, two-way radios, communicators, and the like. Wireless data access is supported by many wireless networks, including, but not limited to, CDPD, CDMA, GSM, PDC, PHS, TDMA, FLEX, ReFLEX, iDEN, TETRA, DECT, DataTAC, Mobitex, EDGE and other 2G, 3G, 4G and LTE technologies, and it operates with many handheld device operating systems, such as PalmOS, EPOC, Windows CE, FLEXOS, OS/9, JavaOS, iOS and Android. Typically, these devices use graphical displays and can access the Internet (or other communications network) on so-called mini- or micro-browsers, which are web browsers with small file sizes that can accommodate the reduced memory constraints of wireless networks. In a representative embodiment, the mobile device is a cellular telephone or smart phone that operates over GPRS (General Packet Radio Services), which is a data technology for GSM networks. In addition to a conventional voice communication, a given mobile device can communicate with another such device via many different types of message transfer techniques, including SMS (short message service), enhanced SMS (EMS), multi-media message (MMS), email WAP, paging, or other known or later-developed wireless data formats. Although many of the examples provided herein are implemented on a mobile device, the examples may similarly be implemented on any suitable computing device.

Operating environments in which embodiments of the presently disclosed subject matter may be implemented are also well-known. In a representative embodiment, a computing device, such as a mobile device, is connectable (for example, via WAP) to a transmission functionality that varies depending on implementation. Thus, for example, where the operating environment is a wide area wireless network (e.g., a 2.5G network, a 3G network, or a 4G network), the transmission functionality comprises one or more components such as a mobile switching center (MSC) (an enhanced ISDN switch that is responsible for call handling of mobile subscribers), a visitor location register (VLR) (an intelligent database that stores on a temporary basis data required to handle calls set up or received by mobile devices registered with the VLR), a home location register (HLR) (an intelligent database responsible for management of each subscriber's records), one or more base stations (which provide radio coverage with a cell), a base station controller (BSC) (a switch that acts as a local concentrator of traffic and provides local switching to effect handover between base stations), and a packet control unit (PCU) (a device that separates data traffic coming from a mobile device). The HLR also controls certain services associated with incoming calls. Of course, the presently disclosed subject matter may be implemented in other and next-generation mobile networks and devices as well. The mobile device is the physical equipment used by the end user, typically a subscriber to the wireless network. Typically, a mobile device is a 2.5G-compliant device or 3G-compliant device (or the proposed 4G-compliant device) that includes a subscriber identity module (SIM), which is a smart card that carries subscriber-specific information, mobile equipment (e.g., radio and associated signal processing devices), a user interface (or a man-machine interface (MMI), and one or more interfaces to external devices (e.g., computers, PDAs, and the like). The mobile device may also include a memory or data store.

Figure 1:
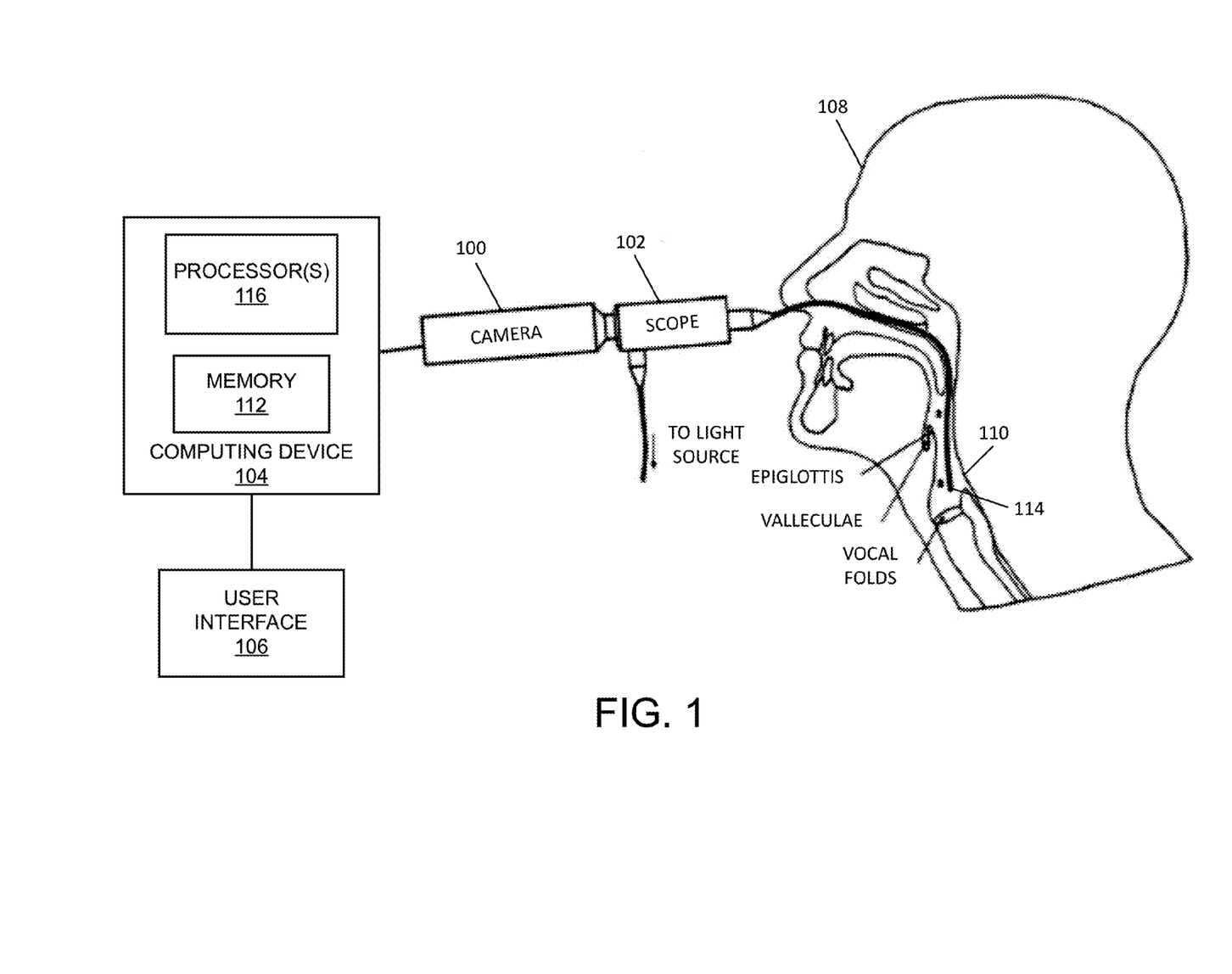
FIG. 1 is a schematic diagram of an example system for use by a medical practitioner to observe and analyze swallowing of an individual in accordance with embodiments of the present disclosure.

The present disclosure is now described in more detail. For example, FIG. 1 illustrates a schematic diagram of an example system for use by a medical practitioner to observe and analyze swallowing of an individual in accordance with embodiments of the present disclosure. Referring to FIG. 1, the system includes an image capture device 100, an intubating scope 102, and a computing device 104 operably connected to a user interface 106. The system may be used by a medical practitioner, such as a speech-language pathologist, to intubate an individual's 108 throat 110 for capture of images or video by the image capture device 100. The image capture device 100 may be operably connected to the computing device 104 for receipt of the captured image(s) or video by the computing device 104. The computing device 104 may suitably store the captured image(s) or video in its memory 112. Alternatively, the captured image(s) or video may be stored at a remote location, such as, but not limited to, at a server farm. As depicted in the figure, an end 114 of the scope 102 may be suitably positioned by the medical practitioner near the vocal folds of the individual 108 for capture of images or video of this portion of the throat's interior. The computing device 104 may suitably control the image capture device 100 to capture images or video during all or some of the phases of swallowing. For example, images or video may be captured during the pharyngeal phase.

The image capture device 100 may include any suitable camera operably connected to the intubating scope 102 for capture of images or video. In this example, the camera is positioned at an end of the scope 102 distal from the end 114. Fiber optics may be used to carry light from the throat's interior to the camera, and to deliver light from a light source to the throat's interior for illuminating the interior. In another example, the camera may be suitably affixed to the end 114 of the scope 102. The configuration of the image capture device 100 and scope 102 for capturing images and/or video of the throat's interior will be understood to those of skill in the art.

The computing device 104 is configured to receive the captured one or more images, analyze the one or more images to measure an amount of tissue covered by bolus in the one or more images, and present information indicating the measure of the amount of tissue covered by bolus. The computing device 104 may include suitable hardware, software, firmware, or combinations thereof for implementing the functionality described herein. For example, the computing device 104 may include one or more processors 116 and the memory 112. The memory 112 may store executable instructions for implementation by the processor(s) 116 for implementing the functionality described herein.

The user interface 106 may include one or more devices or components for receiving user input and for presenting information, graphics, and the like in accordance with embodiments of the present disclosure. For example, the user interface 106 may include a keyboard, a mouse, a display, a printer, and the like. These components may be operably connected to the computing device 104 as will be understood by those of skill in the art.

Figure 2:
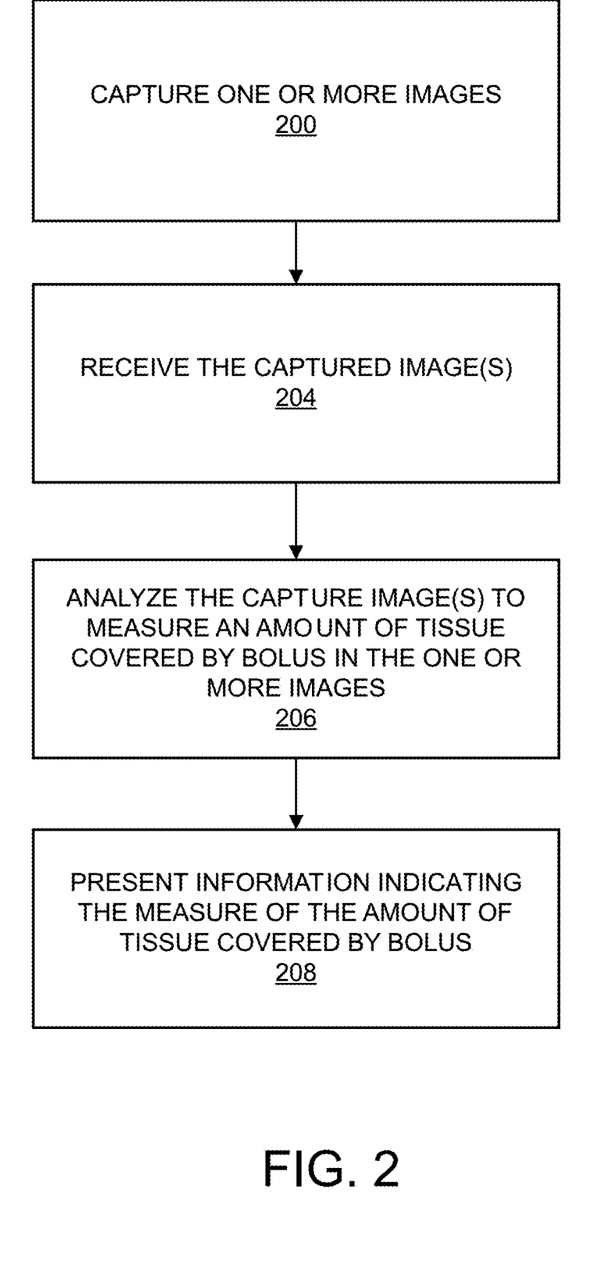
FIG. 2 is a flow chart of an example method use to observe and analyze swallowing of an individual in accordance with embodiments of the present disclosure.

Now turning to FIG. 2, this figure illustrates a flow chart of an example method used to observe and analyze swallowing of an individual in accordance with embodiments of the present disclosure. This example method is described in this example as being implemented by the system shown in FIG. 1, although it should be understood that the method example may alternatively implemented by any other suitable system.

The method of FIG. 2 includes capturing 200 one or more images. For example, the camera 100 and the scope 102 may be operated to capture images and/or video of the interior of the throat 110 shown in FIG. 1. The images and video may be captured during the pharyngeal phase of swallowing of bolus by the individual 108. It will be understood by skilled medical practitioners that the bolus may include foodstuff and/or liquid prepared for observing the individual's swallowing. Prior to being given to the individual 108 for swallowing, the bolus may be covered at least partially with blue or green food coloring such that the bolus may be easily identified in captured images or video based on the coloring. Techniques for coloring foodstuffs and liquid for identification should be understood by those of skill in the art.

The method of FIG. 2 includes receiving 202 the captured image(s). Continuing the aforementioned example, the computing device 104 may receive the captured images or video. In this example, the computing device 104 is suitably connected to a camera for received of the captured images or video.

The method of FIG. 2 includes analyzing the captured image(s) to measure an amount of tissue covered by bolus in the one or more images. Continuing the aforementioned example, the computing device may analyze the captured images or video to measure an amount of tissue covered by bolus viewable in the images or video. As an example, the computing device may determine a color category of each pixel in each of the captured images (or frames of video); determine, for each color category, the number of pixels having a color within the color category; and present information indicating a ratio of the color categories to each other. The color categories may include blue, green, and red. In accordance with embodiments, the computing device may determine the number of pixels in the blue and green color categories; determine the number of pixels in the red color category; and present information indicating a ratio of the numbers of pixels in the blue and green color categories to the number of pixels in the red color category.

The method of FIG. 2 includes presenting information indicating the measure of the amount of tissue covered by bolus. Continuing the aforementioned example, the computing device 104 may control a display of the user interface 106 to display the captured images or video. Further, the computing device may control the display to display information indicating the measure of the amount of tissue covered by bolus.

In accordance with embodiments, the computing device 104 may be configured to, for each image: determine the number of pixels in the blue and green color categories; and present information indicating a percentage of pixels in the blue and green color categories. In other embodiments, the computing device 104 may be configured to, for each image:

determine the number of pixels in the red color category; and present information indicating a percentage of pixels in the red color category.

Figure 3A:
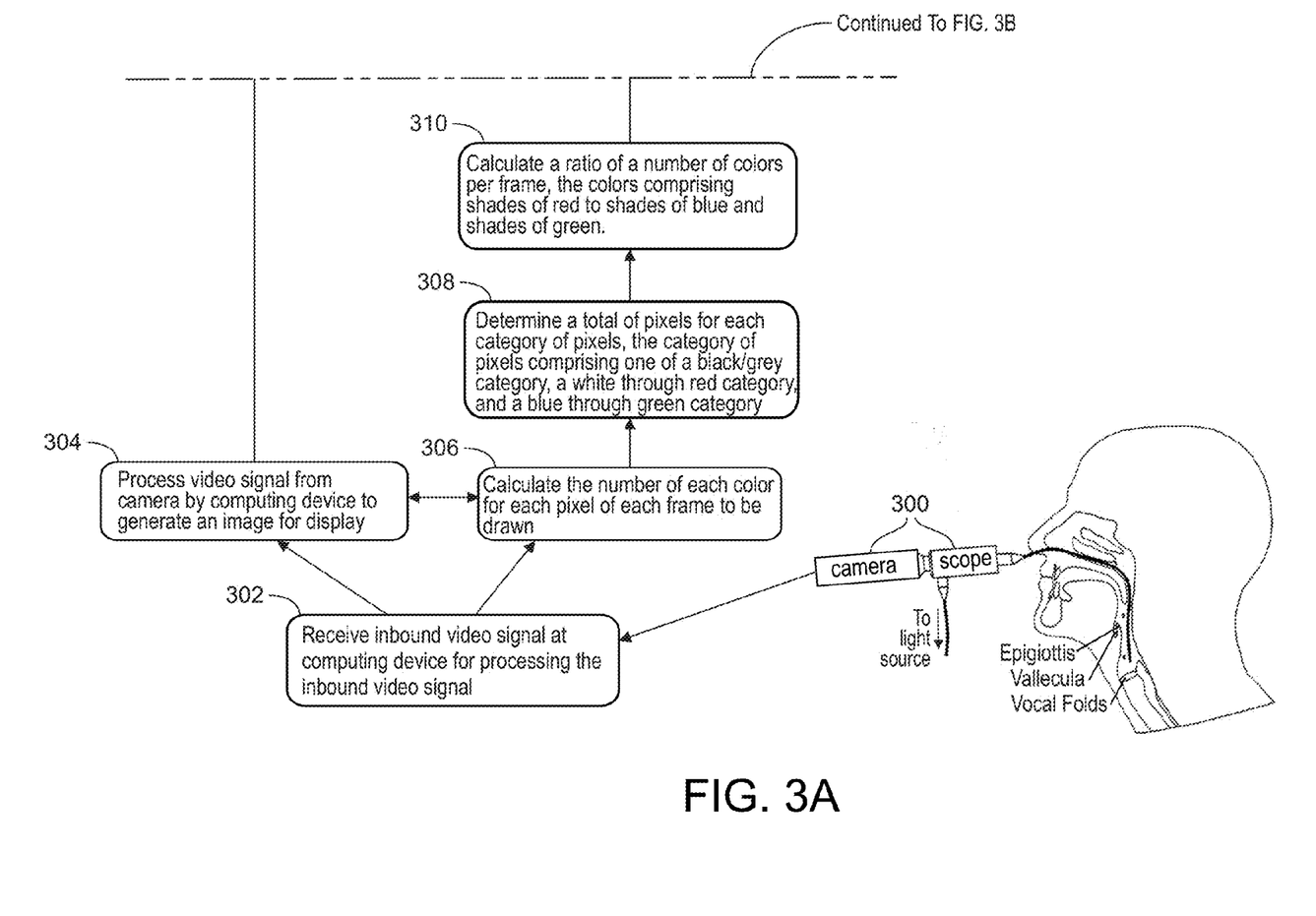
FIG. 3A-3B is a schematic diagram showing an example method and system for use by a medical practitioner to observe and analyze swallowing of an individual in accordance with embodiments of the present disclosure.
Figure 3B:
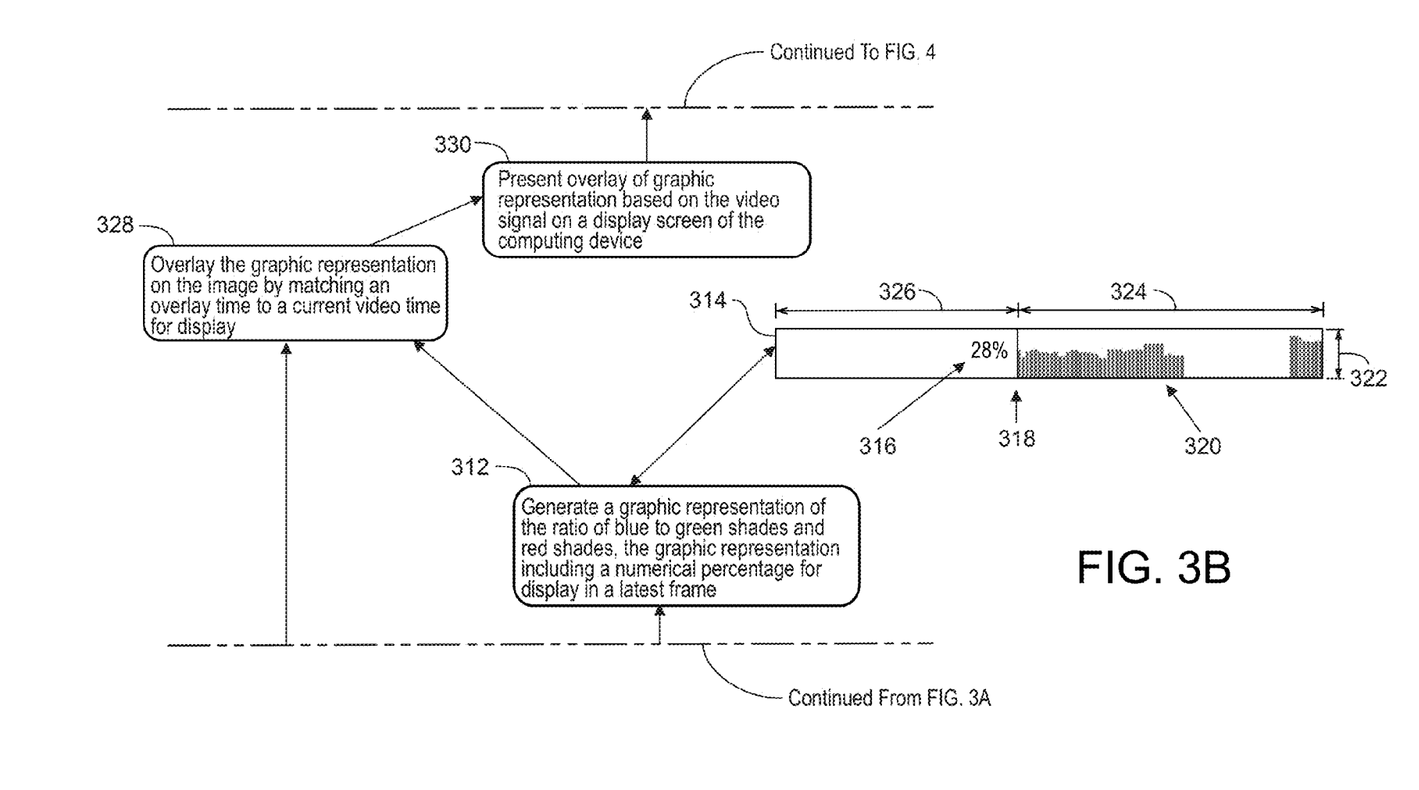
Figure 4:
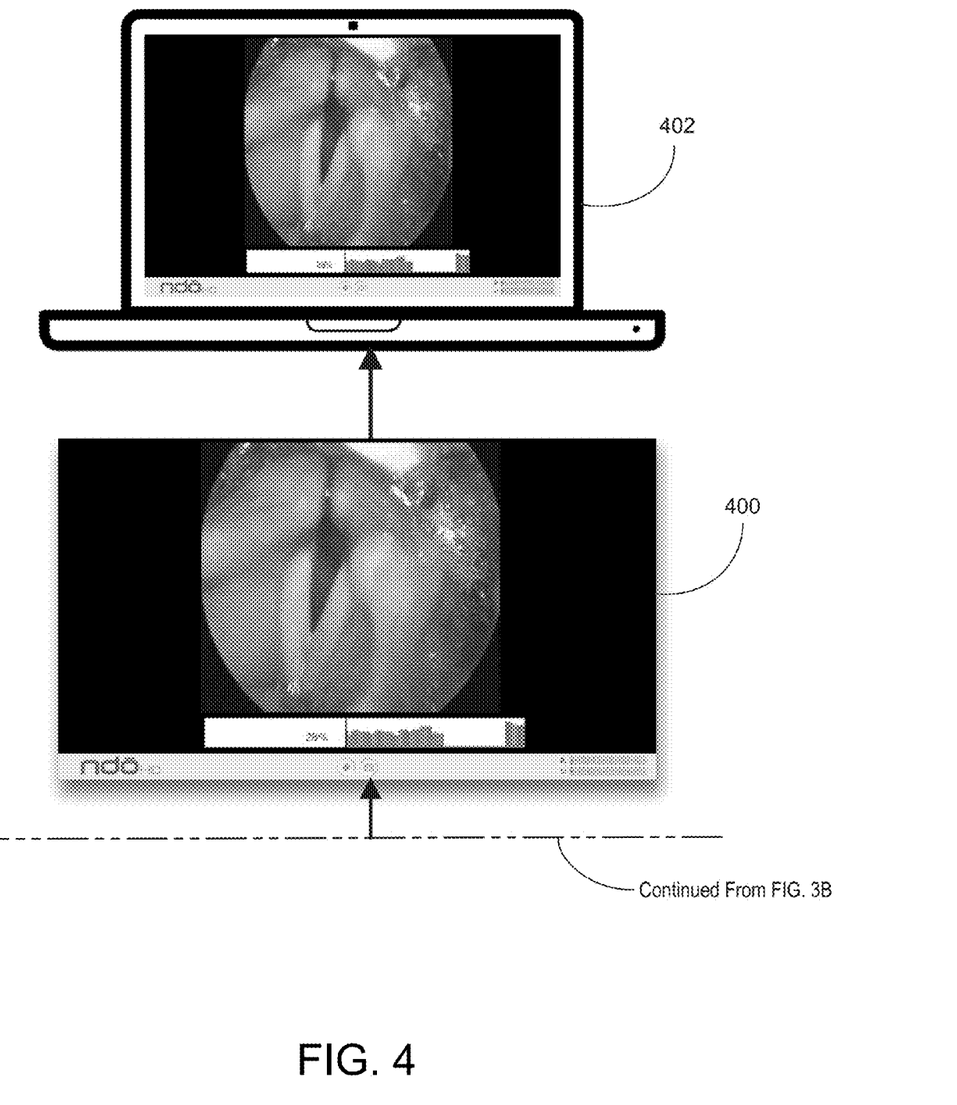
FIG. 4 is a schematic diagram showing example user interface for display on a computing device for use by a medical practitioner to observe and analyze swallowing of an individual in accordance with embodiments of the present disclosure.

FIGS. 3A and 3B illustrate a schematic diagram showing an example method and system for use by a medical practitioner to observe and analyze swallowing of an individual in accordance with embodiments of the present disclosure. Referring to FIGS. 3A and 3B, the diagram includes a flow chart describing additional details of the example method of FIG. 2. The method may be implemented is associated with the system 300 of FIG. 3A. FIG. 3A depicts a system 300 including a fiber scope operatively connected to a chip camera or chip tip videoscope. The camera or video scope may be transnasally inserted in order to assess pharyngeal phase swallow function while the subject is given food and/or liquid boluses that are colored either blue or green. It should be noted that system 300 may be the system shown in FIG. 1 or any other suitable system for implementing the functionality depicted in FIGS. 3A-3B. Example graphical overlays and screen displays are illustrated in FIG. 4.

In accordance with embodiments, the method of FIGS. 3A and 3B may include receiving 302 an inbound video signal at a computing device for processing the inbound video signal. For example, the computing device 104 of FIG. 1 may receive an inbound video signal from the camera of system 300 of FIG. 3A for processing the inbound video signal. Although not depicted in FIG. 3A, it should be understood that computing device 104 may be a part of system 300 or operatively coupled to system 300. The computing device 104 may also be any other suitable computing device for implementing functionality described herein. Also in accordance with embodiments, the method may include processing 304 a video signal from the camera by the computing device to generate an image for display. For example, the computing device 104 of FIG. 1 may process a video signal from the camera of system 300 to generate an image or video for display. The video signal is received by the computing device for processing so that the video image can be displayed onscreen to the user of the computing device so that the image can be analyzed to display the amount of tissue that is covered by residual bolus. Also in accordance with embodiments, the method may include determining the color to be displayed at each pixel of the image on the display.

The method of includes calculating 306 the number of each color for each pixel of each frame to be drawn. For example, the computing device 104 of FIG. 1 may calculate the number of each color for each pixel of each frame to be drawn. In accordance with embodiments, the method may include itemizing, frame by frame of the video signal, all or many of the colors that have been sent to the computing device using color codes that are associated with each color that a display is capable of displaying. Also in accordance with embodiments, the method may include categorizing and counting the instances of each color according to the native color profile that is transmitted by the video source and its associated code. For example, the native color profile may comprise an RGB ratio for an instance of a color. Continuing this example, for 63 pixels of a current frame, a color with an RGB ratio of R:81, G:142, and B:22 may occur in the current frame of a video signal. The method may also include repeating the step of categorizing and counting for each color that is received at the computing device from the video source for each frame of the video signal.

FIG. 3A also illustrates determining 308 a total of pixels for each category of pixels, the category of pixels comprising one of a black/grey category, a white through red category, and a blue through green category. For example, the computing device 104 of FIG. 1 may determine total of pixels for each category of pixels, the category of pixels comprising one of a black/grey category, a white through red category, and a blue through green category. For example, after having analyzed each pixel for a frame of video that is to be displayed, the computing device 104 may calculate the number of occurrences for each color. The computing device 104 may sum the total number of occurrences for each color that fit within the following color ranges: white, shades of black, shades of red, and the sum of shades of blue and shades of green.

The method may include calculating 310 a ratio of a number of colors per frame, the colors comprising shades of red to shades of blue and shades of green as illustrated in FIG. 3A. For example, the computing device 104 may calculate a ratio of a number of colors per frame, the colors comprising shades of red to shades of blue and shades of green. In accordance with embodiments, the ratio may comprise a total number of shades of blues plus shades of greens to shades of reds in a given frame. For example, the ratio may be computed using the following formula: Sum (blues+greens)÷Sum (reds)=% blue-green in a given frame. In accordance with embodiments, the method may include displaying the resultant percentage to the user in both a graphical and numerical form to give the user a measure of the amount of bolus residual coating that are in a given frame.

Now turning to FIG. 3B, the method includes generating 312 a graphic representation of the ratio of blue to green shades and red shades. The graphic representation may include a numerical percentage for display in a latest frame. For example, computing device 104 of FIG. 1 may generate a graphic representation 314 of FIG. 3B of the ratio of blue to green shades and red shades, the graphic representation 314 including a numerical percentage 316 for display in a latest frame. It should be noted that the graphic representation 314 is illustrative only and the graphic representation of the present disclosure described herein is not limited to example provided in FIG. 3B.

The method may also include adding a vertical bar to the graphic representation as each frame is analyzed. For example, graphic representation 314 includes an added vertical bar at a current frame 318 as each frame is analyzed. In accordance with embodiments, each bar of the graphic representation represents one frame of the analyzed video signal. For example, each bar 320 of the graphical representation represents one frame of the analyzed video signal.

To the user, this can create the effect of vertical bars of the graphical representation marching left to right across the bottom of the user's screen as each frame is analyzed. In accordance with embodiments, a time period of frames is to be displayed at all times and overlaid into the video image. For example, graphic presentation 314 of FIG. 3B comprises a time period 324 of frames to be displayed at all times. In this example, time period 324 represents approximately two seconds worth of video signal. Typical video frame rates are about 30 fps. Therefore, the horizontal access of the graphical representation may accommodate up to 60 instances of vertical bars to represent blue-green ratios at a typical frame rate of 30 fps. However, it should be noted that the time period of frames to be displayed in the present disclosure may be based on the frame rate of the incoming video signal.

In accordance with embodiments, the graphical representation may comprise a vertical axis representing a range of values of the blue-green ratios. For example, FIG. 3B illustrates graphical representation 314 comprises a vertical axis 322 representing a range of the blue-green ratios. Vertical axis 322 represents a range of 0% to 100% ratio values of blue-green ratios. Also in accordance with embodiments, the graphical representation may show a time period of upcoming frames of the analyzed video signal. For example, FIG. 3B illustrates graphical representation 314 comprises a time period 326 of upcoming frames of upcoming frames. In this example, time period 326 also represents approximately two seconds worth of video signal. However, it is noted that the time period of upcoming frames to be displayed in the present disclosure may be based on the frame rate of the incoming video signal.

It should also be noted that the graphic representation of the blue-green ratio may be displayed as a "gas gauge" or "wave" form with fluctuations plotted on a frame by frame basis similarly as described in the bar graph implementation above.

With continuing reference to FIG. 3B, the method includes overlaying 328 the graphic representation on the image by matching an overlay time to a current video frame for display. For example, the computing device 104 of FIG. 1 may overlay the graphic representation 314 on the image by matching an overlay time to a current video frame for display. For example, FIG. 4 illustrates a graphical representation overlaid on an image 400 of a current video frame of the video signal. In accordance with embodiments, the method may include positioning the graphical representation below or above the central video image that is generated by the camera. For example, FIG. 4 illustrates the graphical representation is positioned below the central video image. The user can elect to have the graphical representation below or above the central video image by choosing a setting in preference pane of the application.

FIG. 3B further illustrates the method may include presenting 330 the overlay of the graphic representation based on the video signal on a display screen of the computing device. For example, FIG. 4 illustrates presenting the overlay of the graphic representation based on the video signal on a display screen of computing device 402. Although FIG. 4 illustrates computing device 402 as a laptop computing device, it should be noted that the present disclosure is not limited to such an example, but is only provided for illustrative purposes.

Figure 5:
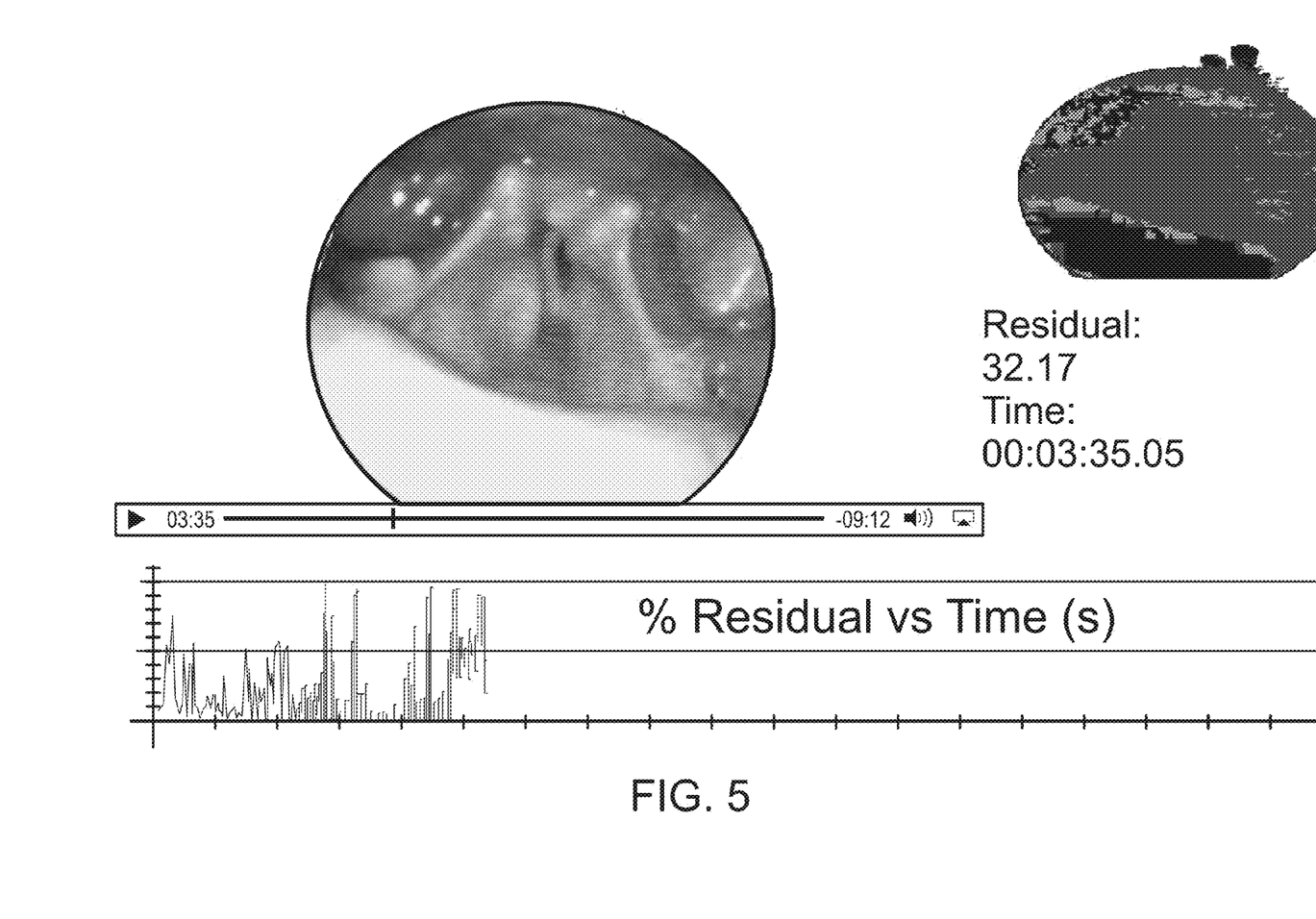
FIG. 5 is an example user interface for display on a computing device for use by a medical practitioner to observe and analyze swallowing of an individual in accordance with embodiments of the present disclosure.

FIG. 5 illustrates example user interface for display on a computing device for use by a medical practitioner to observe and analyze swallowing of an individual in accordance with embodiments of the present disclosure. An example benefit is that the medical practitioner is provided relevant clinical information on which to make diagnostic decisions and treatment planning. Additionally, the information can be used to determine efficacy of ongoing treatment. As shown in FIG. 5, a user interface of the computing device may include displaying a current video frame during image capture. In another example, the user interface of the computing device may include displaying a current video frame during playback of a previously recorded video signal. For example, FIG. 5 illustrates a playback control panel underneath the displayed current video frame of the user interface. Although the example provided in FIG. 5 illustrates the playback control of the video signal underneath the current video frame in the user frame, it should be understood that the control panel may be located in a different area of the user interface to control playback of the previously recorded video signal.

FIG. 5 also illustrates the user interface may include a graphical representation of a ratio of blue to green shades and red shades in the current video frame. For example, FIG. 5 illustrates a graphical representation of the ratio at the bottom of the user interface. In this example, the graphical representation of FIG. 5 includes a spike style graph of the percentage of residual bolus over time in the real-time of captured video signal. Although the example provided in FIG. 5 illustrates the graphical representation including a spike style graph, it should be understood that the graphical representation may be similar as to the example provided in FIG. 4.

In accordance with embodiments, the user interface may also include a pictorial representation of the pixel color distribution within the current video frame. In accordance with embodiments, the pictorial representation may include a heat map of the blue, green, and red pixels within the current video frame. For example, FIG. 5 illustrates in the top right corner of the user interface a pictorial representation of the pixel color distribution within the current video frame displayed in FIG. 5. In this example, the pictorial representation comprises a heat map of the blue, green, and red pixels within the current video frame displayed in this user interface of FIG. 5. An example benefit of the heat map is that the medical practitioner is provided relevant clinical information on which to make diagnostic decisions and treatment planning. Additionally, the information can be used to determine efficacy of ongoing treatment.

In accordance with embodiments, the user interface may also include a numerical percentage representation of the residual bolus for the current video frame. For example, FIG. 5 illustrates the user interface may include a numerical percentage representation of the residual bolus beneath the pictorial graphical representation of the residual bolus. Although the example provided in FIG. 5 illustrates the numerical percentage representation beneath the pictorial representation, it should be understood that the numerical percentage representation may be located in an alternative location in the user interface.

Figure 6:
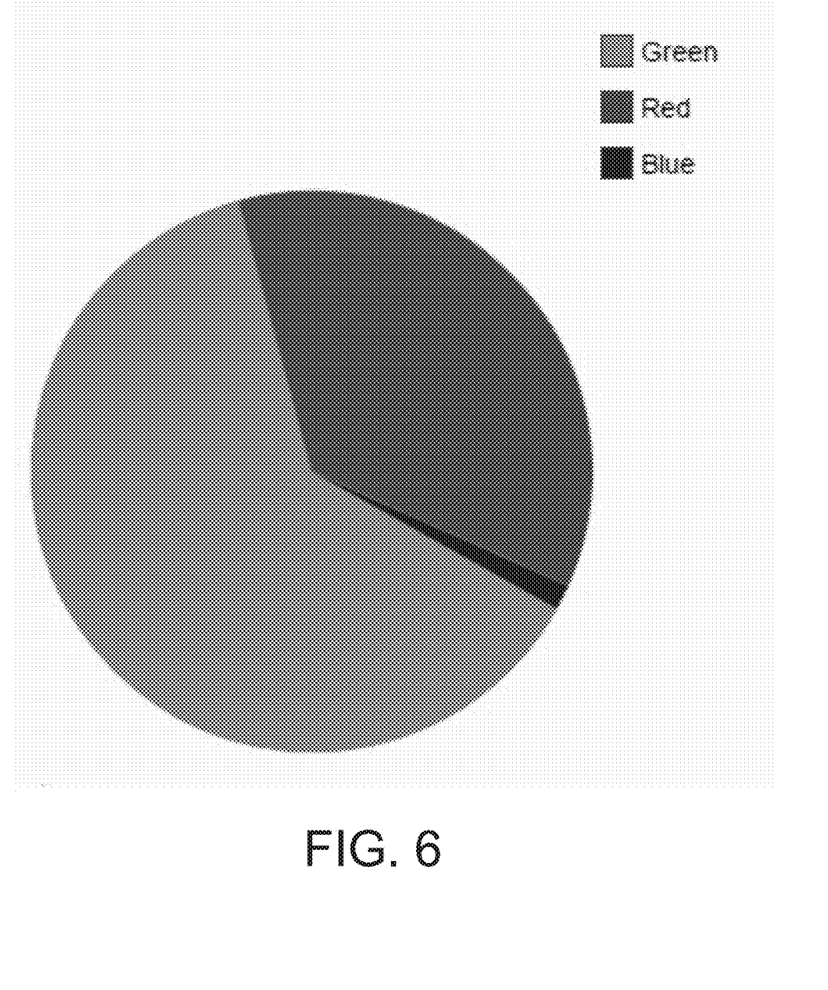
FIG. 6 is an example graphic illustration demonstrating a ratio of blue, green, and red pixels in a given frame in accordance with embodiments of the present disclosure.

FIG. 6 illustrates a graphic illustration of an example pie chart showing a ratio of blue, green, and red pixels in a given frame in accordance with embodiments of the present disclosure. An example benefit of showing the pie chart is that the medical practitioner is provided relevant clinical information on which to make diagnostic decisions and treatment planning. Additionally, the information can be used to determine efficacy of ongoing treatment. A graphical representation of a given frame may be graph, bar graph, the like, or any other suitable technique for presenting data as will be understood by those of skill in the art.

In accordance with embodiments, the functions described herein may be implemented on a live stream of video or recorded video. The functionality described herein may be implemented on the live stream video and provide display results to a user in real time. Live color analysis of the video stream can enable a medical practitioner to have immediate access to information that can drive patient care decisions. Analysis of pre-recorded patient examinations can give medical practitioners access to analysis that was not previously available such as clinical peer review, treatment plan review, peer reviewed research for developing new diagnostic methodologies.

It is noted that the computing device implemented the functionality described herein may be communicating with any suitable computing device such as, but not limited to, a smartphone, router, laptop computer, desktop computer, or the like.

The present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the present disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system comprising:
an intubating scope and image capture device configured to capture a video of an interior of a subject's throat during swallowing of bolus;
a computing device including at least one processor and memory configured to:
receive the captured video;
determine a color category of pixels in frames of the video;
determine, for each color category, the number of pixels having a color within the color category to produce information indicating a measure of an amount of tissue covered by bolus during the swallowing of the bolus;
determine, for each color category, the number of pixels having a color within the color category to produce information indicating a measure of an amount of tissue not covered by bolus during the swallowing of the bolus; and
present, during the swallowing of the bolus, the information indicating the measure of the amount of tissue covered by bolus and the amount of tissue not covered by bolus.

2. The system of claim 1, wherein the intubating scope is inserted transnasally into the interior of the subject's throat.

3. The system of claim 1, wherein the video is captured during pharyngeal phase swallowing.

4. The system of claim 1, wherein the bolus is colored blue or green.

5. The system of claim 1, wherein the computing device is configured to:
determine a color category of each pixel in each frame of the video;
determine, for each color category, the number of pixels having a color within the color category; and
present information indicating a ratio of the color categories to each other.

6. The system of claim 5, wherein the color categories comprise blue, green, and red.

7. The system of claim 6, wherein the computing device is configured to:
determine the number of pixels in the blue and green color categories;
determine the number of pixels in the red color category; and
present information indicating a ratio of the numbers of pixels in the blue and green color categories to the number of pixels in the red color category.

8. The system of claim 1, wherein the computing device comprises a display configured to display the video.

9. The system of claim 1, wherein the computing device comprises a display configured to display information indicating the measure of the amount of tissue covered by bolus.

10. The system of claim 1, wherein the computing device is configured to:
for each image, determine the number of pixels in the blue and green color categories; and
for each image, present information indicating a percentage of pixels in the blue and green color categories.

11. The system of claim 1, wherein the computing device is configured to:
for each image, determine the number of pixels in the red color category; and
for each image, present information indicating a percentage of pixels in the red color category.

12. A method comprising:
receiving video one of an interior of a subject's throat during swallowing of bolus;
determining a color category of pixels in frames of the video;
determining, for each color category, the number of pixels having a color within the color category to produce information indicating a measure of an amount of tissue covered by bolus during the swallowing of the bolus;
determining, for each color category, the number of pixels having a color within the color category to produce information indicating a measure of an amount of tissue not covered by bolus during the swallowing of the bolus; and
presenting, during the swallowing of the bolus, the information indicating the measure of the amount of tissue covered by bolus and the amount of tissue not covered by bolus.

13. The method of claim 12, further comprising inserting an intubating scope into the interior of the subject's throat for capture of the video via an image capture device.

14. The method of claim 12, further comprising capturing the video during pharyngeal phase swallowing.

15. The method of claim 12, wherein the bolus is colored blue or green.

16. The method of claim 12, further comprising:
determining a color category of each pixel in each frame of the video;
determining, for each color category, the number of pixels having a color within the color category; and
presenting information indicating a ratio of the color categories to each other.

17. The method of claim 16, wherein the color categories comprise blue, green, and red.

18. The method of claim 17, further comprising:
determining the number of pixels in the blue and green color categories;
determining the number of pixels in the red color category; and
presenting information indicating a ratio of the numbers of pixels in the blue and green color categories to the number of pixels in the red color category.

19. The method of claim 12, further comprising displaying the video.

20. The method of claim 12, further comprising displaying information indicating the measure of the amount of tissue covered by bolus.

21. The method of claim 12, further comprising:
for each image, determining the number of pixels in the blue and green color categories; and
for each image, presenting information indicating a percentage of pixels in the blue and green color categories.

22. The method of claim 12, further comprising:
for each image, determining the number of pixels in the red color category; and
for each image, presenting information indicating a percentage of pixels in the red color category.

23. A computer program product for analyzing swallowing, the computer program product comprising a computer readable storage medium having program instructions embodied therewith, the program instructions executable by a computing device to cause the computing device to:

receive, by the computing device, video of an interior of a subject's throat during swallowing of bolus;
determine, by the computing device, a color category of pixels in frames of the video;
determine, by the computing device and for each color category, the number of pixels having a color within the color category to produce information indicating a measure of an amount of tissue covered by bolus during the swallowing of the bolus;
determine, by the computing device and for each color category, the number of pixels having a color within the color category to produce information indicating a measure of an amount of tissue not covered by bolus during the swallowing of the bolus; and
present, by the computing device and during swallowing of the bolus, the information indicating the measure of the amount of tissue covered by bolus and the amount of tissue not covered by bolus.

\* \* \* \* \*